(12) United States Patent
Garlick et al.

(10) Patent No.: US 6,757,215 B2
(45) Date of Patent: Jun. 29, 2004

(54) APPARATUS AND PROCESS MODIFICATIONS IN ULTRASONIC HOLOGRAPHY TO IMPROVE IMAGE QUALITY

(75) Inventors: George F. Garlick, Richland, WA (US); Jerod O. Shelby, Richland, WA (US); Ronald L. Shelby, Richland, WA (US)

(73) Assignee: Advanced Imaging Technologies, Inc., Preston, WA (US)

( * ) Notice: Subject to any disclaimer, the term of this patent is extended or adjusted under 35 U.S.C. 154(b) by 25 days.

(21) Appl. No.: 10/319,400

(22) Filed: Dec. 13, 2002

(65) Prior Publication Data

US 2004/0037164 A1 Feb. 26, 2004

Related U.S. Application Data

(63) Continuation-in-part of application No. 09/589,855, filed on Jun. 8, 2000, now Pat. No. 6,590,830.

(51) Int. Cl.[7] .......................... G01N 29/04; G03H 3/00
(52) U.S. Cl. ........................... 367/8; 359/901; 73/603; 73/605; 600/437
(58) Field of Search ..................... 367/7, 8, 10; 73/603, 73/605; 359/901; 600/437

(56) References Cited

U.S. PATENT DOCUMENTS

| | | | |
|---|---|---|---|
| 3,564,905 A | 2/1971 | Brenden et al. | 73/67.5 |
| 3,742,439 A | 6/1973 | Sheridon | 340/5 |
| 3,760,344 A | 9/1973 | Hildebrand | 340/5 H |
| 3,879,989 A | 4/1975 | Brenden | 73/67.5 |
| 3,899,767 A * | 8/1975 | Jones | 367/11 |
| 3,911,729 A | 10/1975 | Collins | 73/67.5 H |
| 3,983,529 A | 9/1976 | Langlois | 340/5 |
| 4,028,934 A | 6/1977 | Sollish | 73/67.8 S |
| 4,478,481 A | 10/1984 | Fusek et al. | 350/3.83 |
| 4,531,410 A | 7/1985 | Crostack | 73/603 |
| 4,662,222 A | 5/1987 | Johnson | 73/602 |
| 5,179,455 A | 1/1993 | Garlick | 359/9 |
| 5,212,571 A | 5/1993 | Garlick et al. | 359/9 |
| 5,235,553 A | 8/1993 | Garlick et al. | 367/7 |
| 5,329,202 A | 7/1994 | Garlick et al. | 310/334 |
| 5,329,817 A | 7/1994 | Garlick et al. | 73/605 |
| 5,796,003 A | 8/1998 | Sandhu et al. | 73/603 |
| 5,999,836 A | 12/1999 | Nelson et al. | 600/407 |
| 6,590,830 B1 * | 7/2003 | Garlick et al. | 367/8 |
| 2004/0037164 A1 * | 2/2004 | Garlick et al. | 367/8 |

OTHER PUBLICATIONS

Knoll, A.C., "*Ultrasonic Holography Techniques for Localizing and Imaging Solid Objects*", IEEE transactions on Robotics an Automation, vol. 7, No. 4, Aug. 4, 1991.

\* cited by examiner

Primary Examiner—John B. Sotomayor
(74) Attorney, Agent, or Firm—Seed IP Law Group PLLC

(57) ABSTRACT

A method and apparatus for generating an acoustic holographic image having a plurality of pulses with different characteristic parameters from each other. More particularly, a sequence contains a plurality of pulses which have different characteristic parameters from each other. An image is created for each sequence and the effect of each pulse in creating the image is varied based on the variation of the characteristic parameter for each pulse. A selectively enhanced acoustic image is thereby obtained.

15 Claims, 11 Drawing Sheets

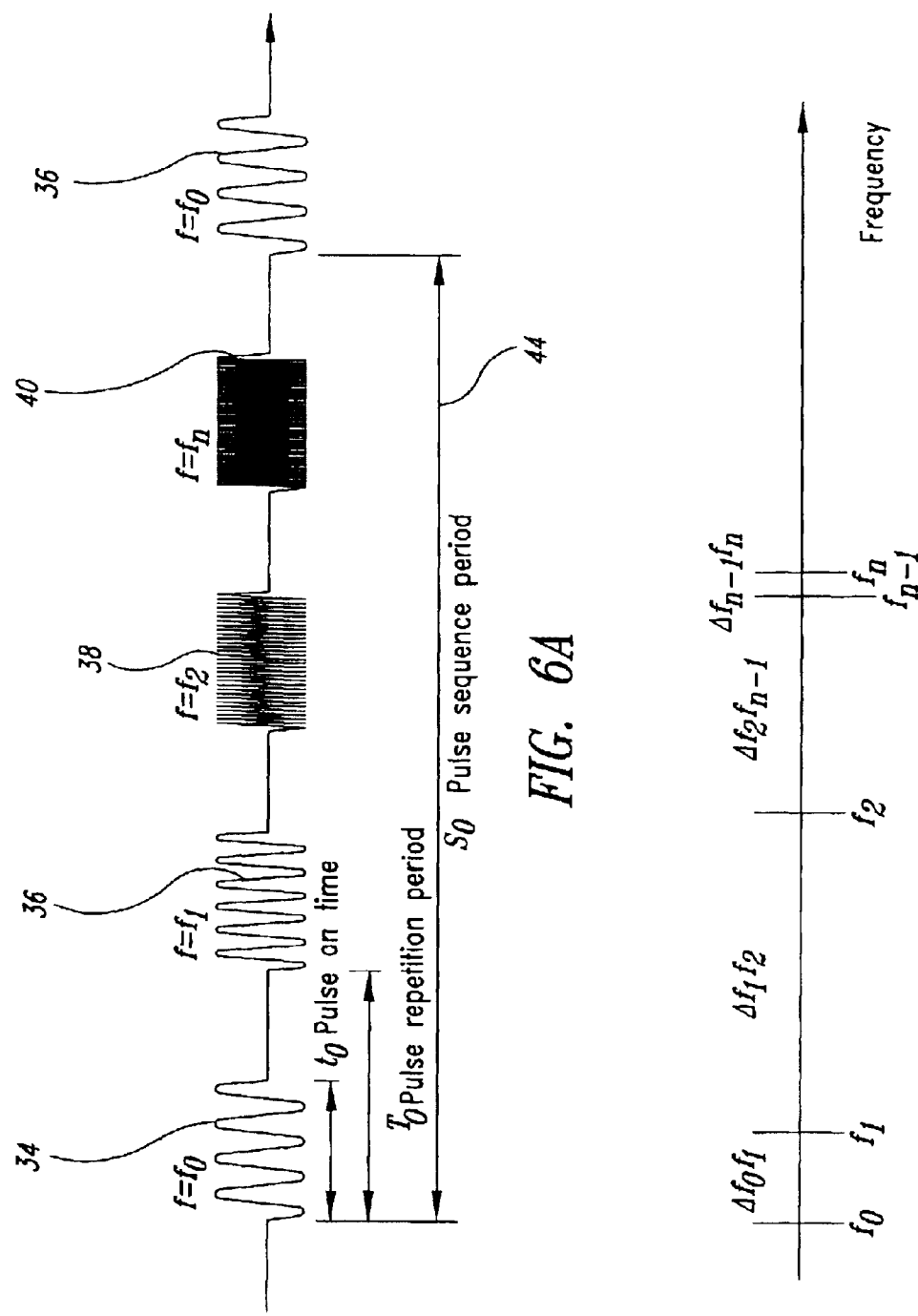

APPARATUS AND PROCESS MODIFICATIONS IN ULTRASONIC HOLOGRAPHY TO IMPROVE IMAGE QUALITY

CROSS-REFERENCE TO RELATED APPLICATION

This application is a continuation-in-part of U.S. patent application Ser. No. 09/589,855, filed Jun. 8, 2000, now U.S. Pat. No. 6,590,830, which application is incorporated herein by reference in its entirety.

FIELD OF THE INVENTION

The present invention provides a series of process and apparatus modifications to ultrasonic holography imaging systems that each or together function to enhance image quality of ultrasonic holography images. Specifically, the present invention provides a process and apparatus for generating multiple exposure ultrasonic holography images generated from selected orientations, each of which can provide multiple images, utilizing multiple intensities, and multiple frequencies from each orientation. The inventive process and apparatus for providing multiple view, multiple angle, and multiple frequency or intensity transmissive ultrasound imaging of the internal structures of an object provides an object sound (ultrasound or ultrasonic energy) intensity of equal or near equal intensity across the entire field of the object, such as a human breast.

BACKGROUND OF THE INVENTION

A central element field of holography is fulfilled by combining or interfering an object wave or ultrasonic energy with a reference wave or ultrasonic energy to form an interference pattern referred to as the hologram. A fundamental requirement for the forming of the hologram and the practice of holography is that the initial source of the object wave and reference wave or energy are coherent with respect to the other wave. All parts of both the object wave and the reference wave are of the same frequency and of a defined orientation (a fixed spatial position and angle between the direction of propagation of the two sources). When performing holography the object wave is modified by interference with structure within the object of interest. As this object wave interacts with points of the object the three-dimensional features of the object impart identifying phase and amplitude changes on the object wave. Since the reference wave is an unperturbed (pure) coherent wave, its interference with the object wave results in an interference pattern which identifies the 3-D positioning and characteristics (ultrasonic absorption, diffraction, reflection, and refraction) of the scattering points of the object.

A second process, (the reconstruction of the hologram) is then performed when a coherent viewing source (usually light from a laser) is transmitted through or reflected from the hologram. The hologram pattern diffracts light from this coherent viewing or reconstructing source in a manner to represent the 3-D nature of the object, as seen by the ultrasonic object wave.

To reiterate, to perform holography coherent wave sources are required. This requirement currently limits practical applications of the practice of holography to the light domain (e.g., a laser light) or the domain of acoustics (sometimes referred to as ultrasound due to the practical application at ultrasonic frequencies), as these two sources are currently the only available coherent energy sources.

Thus, further references to holography or imaging system will refer to the through transmission holographic imaging process that uses acoustical energies usually in the ultrasonic frequency range. In the practice of ultrasound holography, one key element is the source of the ultrasound, such as a large area ultrasound transducer. A second key element is the projection of the object wave from a volume within the object (the ultrasonic lens projection system) and a third is the detector and reconstruction of the ultrasonic hologram into visual or useful format.

Although other configurations can be utilized, a common requirement of the source transducers for both the object and reference waves is to produce a large area plane wave having constant amplitude across the wave front and having a constant frequency for a sufficient number of cycles to establish coherence as compared to another wave of equal characteristics. Such transducers will produce this desired wave if the amplitude of the ultrasound output decreases in a Gaussian distribution profile as the edge of the large area transducer is approached. This decreasing of amplitude reduces or eliminates the "edge effect" from the transducer edge, which would otherwise cause varying amplitude across the wave front as a function distance from the transducer.

In the process of through transmission ultrasonic holographic imaging, an ultrasonic energy pulse from the object transducer progresses through the object, then through an acoustic focusing lens and at the appropriate time, a second pulse of ultrasound is generated from the reference transducer such that the object wave and reference wave arrive at the detector at the same time to create a interference pattern (the hologram). For broad applications, the transducers need to be able to operate at a spectrum or bandwidth of discrete frequencies. Multiple frequencies allow comparisons and integration of holograms taken at selected frequencies to provide an improved image of the subtle changes within the object.

A hologram can also be formed by directing the object wave through the object at different angles to the central imaging axis of the lens means. This is provided by either positioning or rotating the object transducer around the central axis of the lens means or by using multiple transducers positioned such that the path of transmission of the sound is at an angle with respect to the central axis of the lens means.

With a through-transmission imaging system, it is important to determine the amount of resolution in the "z" dimension that is desirable and achievable. Since the holographic process operates without limits of mechanical or electronic devices but rather reconstructs images from wave interactions, the resolution achievable can approach the theoretical limit of one half the wavelength of the ultrasound used. However, it may be desirable to limit the "z" direction image volume so that one can "focus" in on one thin volume slice. Otherwise, the amount of information may be too great. Thus, it is of value to develop a means for projecting a planar slice within a volume into the detector plane. One such means is a large aperture ultrasonic lens means that will allow the imaging system to "focus" on a plane within the object. Additionally, this lens system and the corresponding motorized, computer controlled lens drive will allow one to adjust the focal plane and at any given plane to be able to magnify or demagnify at that z dimension position.

The image is detected and reconstructed at the detector. Standard photographic film may be used for the recording of light holograms and the 3-D image reconstructed by passing laser light through the film or reflecting it from the hologram pattern embossed on the surface of an optical reflective surface and reconstructing the image by reflecting light from the surface. However, there is no equivalent "film" material to record the intricate phase and amplitude pattern of a complex ultrasonic wave. One of the most common detectors uses a liquid-air surface or interface to record, in a dynamic way, the ultrasonic hologram formed. The sound energy at the frequency of ultrasound (above range of human hearing) will propagate with little attenuation through a liquid (such as water) but cannot propagate through air. At these higher frequencies (e.g., above 1 MHz) the ultrasound will not propagate through air because the wavelength of the sound energy is so short ($\lambda$(wavelength)=v/(velocity)/f (frequency)). The density of air (approximately 0.00116 g/cm$^3$) is not sufficient to couple these short wavelengths and allow them to propagate. On the other hand the density of a liquid (e.g., water) is a favorable media to couple and propagate such sound. For example, the velocity of sound in air is approximately 330 meters/second whereas in water it is approximately 1497 meter/second. Thus, for water, both the density (1 g/cm$^3$) and the wavelength (~1.48 mm at 1 MHz) are significantly large such that ultrasound can propagate with little attenuation. Whereas, for air both the density (0.00116 g/cm$^3$) and wavelength (0.33 mm at 1 MHz) are sufficiently small such that the energy at these ultrasonic frequencies will not propagate.

Thus, when ultrasound propagating in a liquid encounters a liquid-air interface the entire amount of the energy is reflected back into the liquid. Since ultrasound (or sound) propagates as a mechanical force it is apparent that the reflection (or changing direction of propagation) will impart a forward force on this liquid air interface. This force, in turn, will distort the surface of the liquid. The amount of surface distortion will depend upon the amplitude of the ultrasound wave at each point being reflected and the surface tension of the liquid. Thus, the pattern of the deformation is the pattern of the phase and amplitude of the ultrasonic wave.

It is in this manner that a liquid-air interface can be commonly used to provide a near real-time recorder ("film equivalent") for an ultrasonic hologram. The shape of the surface deformation on this liquid-air detector is the representation of the phase and amplitude of the ultrasonic hologram formed by the interference of the object and reference ultrasonic waves.

The greatest value of the ultrasonic holographic process is achieved by reconstructing the hologram in a usable manner, usually in light, to make visible the structural nature of the initial object. In the case of a liquid-air interface, the reconstruction to achieve the visible image is accomplished by reflecting a coherent light from this liquid-air surface. This is the equivalent process to reflecting laser light from optically generated hologram that is embossed on the surface of a reflecting material (e.g., thin aluminum film).

The reflected light is diffracted (scattered) by the hologram to diffracted orders, each of which contains image information about the object. These diffracted orders are referred to as ±n th orders. That part of the reconstructing light that does not interact with the hologram is referred to as zero order and is usually blocked so that the weaker diffracted orders can be imaged. The higher the diffracted order the greater the separation angle from the zero order of reflected light.

Once reconstructed, the image may be viewed directly, by means of a video camera or through post processing.

Ultrasonic holography as typically practiced is illustrated in FIG. 1. A plane wave of sound 1a (ultrasound) is generated by the transducer 1 (U.S. Pat. No. 5,329,202 incorporated herein by reference). The sound is scattered (diffracted) by structural points within the object within the focal plane 2. This sound 2a is scattered from the internal object points that lie in the focal plane 15 are focused (projected) into the ultrasonic hologram plane 6. The focusing takes place by use of ultrasonic lens 3 (U.S. Pat. No. 5,235,553 incorporated herein by reference) which focuses the scattered sound into a hologram detector surface 6 and the unscattered sound into a focal point 4. The lens means also allows the imaging process to magnify the image or change focus position (U.S. Pat. No. 5,212,571 incorporated herein by reference). Since the focus point of the unscattered sound 4 is prior to the holographic detector plane 6, this portion of the total sound again expands to form the image from the transparent image contribution (that portion of the sound that transmitted through the object as if it were transparent or semitransparent). In such an application, an ultrasound reflector 5 is generally used to direct the object sound at a different angle (preferably vertically to allow for the holographic detector to have a surface parallel to ground to avoid gravity effects), thus impinging on horizontal detector plane usually containing a liquid which is deformed by the ultrasound reflecting from the liquid-air interface. When the reference wave 8 and the object wave are simultaneous reflected from this detector, the deformation of the liquid-air interface is the exact pattern of the ultrasonic hologram formed by the object wave 1a combined with 2a and the "off-axis" reference wave 8.

This ultrasonic hologram formed in the holographic detector 6 is subsequently reconstructed for viewing by using a coherent light source 9, which may be passed through an optical lens 8, and reflected from the holographic detector surface (U.S. Pat. No. 5,179,455 incorporated herein by reference). This reflected coherent light contains two components. These are A: The light that is reflected from the ultrasound hologram which was not diffracted by the ultrasonic holographic pattern which is focused at position 13 and referred to as undiffracted or zero order light; and B: The light that does get diffracted from/by the ultrasonic hologram is reflected at an "off-axis" angle from the zero order at position 11 and referred to as the "first order" image view when passed through a spatial filter 12. It is noted that this reconstruction method produces multiple diffraction orders each containing the ultrasonic object information. Note also both + and – multiple orders of the diffracted image are present and can be used individually or in combinations to view the optical reconstructed image from the ultrasonically formed hologram by modifying the spatial filter 12 accordingly.

Commercial application of ultrasonic holography has been actively pursued over many years, yet only limited results have been achieved. The application of ultrasonic holography has commercial utility for non-destructive testing of materials and imaging of internal structures in soft tissue. One of the problems often encountered is consistency and quality of images obtained. It is difficult to obtain undistorted images of selected internal structures within objects (such as a human breast) due to interference or shadowing of other out-of-focus structures within the object.

Therefore, there is a need in the art to improve image quality by recognizing and utilizing the effects of diffraction generated by internal structures within the object. This need is particularly strong for breast cancer screening techniques that now utilize invasive mammography (providing the patient with a dose of radiation from X-Ray imaging) and yet do not produce images that are sensitive to detecting some lesions and do not lend a sense of three dimensional structure to breast tissue.

That portion of the ultrasound wave that passes through the imaged object without being scattered by structures within the object can be a major contributor in "semitransparent objects" (that is, an object that scatters a small portion of the sound waves directed at the object). Since many objects of interest can be rather transparent to sound, (e.g. human soft tissue normal structures and tumor tissue of solid tumors) there is formed a bright and strong white light contribution to the image from this sound that does not interfere with the object. When one wants to detect and determine the characteristic of subtle changes in the object (e.g., determining tissue characteristics) this background bright image contribution can overpower the resolution of small and subtle contributions of tissue change. Therefore, there is a need in the art to improve resolution characteristics of transmissive ultrasonic imaging so as to be able to distinguish subtle differences within the object (i.e., so as to be able to image tumor tissue within surrounding soft breast tissue).

In U.S. Pat. No. 5,329,817, an ultrasonic holography imaging process and apparatus embodiment is disclosed that provides for a rotating single ultrasonic transducer (FIGS. 7–9) along with an angled rectangular transducer at an angle θ with respect to the normal plane or axis of the "system" (e.g., centerline of the acoustic lens means). The single ultrasonic transducer element is angled (θ) at an acute incidence angle relative to the optical axis to better remove imaging shadows from out-of-focus (i.e., the focal plane of the object) internal structures of the object.

BRIEF SUMMARY OF THE INVENTION

The present invention provides an ultrasonic holography imaging apparatus comprising:

one or a plurality of ultrasonic transducers directing ultrasonic energy in the form of a wave toward an object to be imaged;

an acoustic lens for focusing the ultrasonic energy to a focal point downstream of a first lens and having a centerline; and a holographic detector having a surface aligned perpendicular to the centerline of the acoustic lens means.

The present invention provides a process for generating an image using an ultrasonic imaging apparatus, comprising the steps of:

providing an object to be internally imaged to be held by the object holder;

transmitting a sequence of individual pulses of ultrasound, each pulse within the sequence comprises: a plurality of cycles of a single frequency (f) of ultrasound, wherein each pulse has a multitude of characteristic parameters; each sequence is composed of a plurality of pulses; and one or more the characteristic parameters is varied from one pulse to another pulse within the same sequence; and imaging the object from a hologram formed in the holographic detection system for each pulse within the sequence.

Preferably, the process further comprises either capturing each separate image for separate analysis for a specific frequency, or averaging a plurality of images from selected frequencies to form a composite image derived from the selected frequencies.

There are a number of characteristic parameters for a pulse of ultrasound used with respect to the present invention. One parameter is the frequency of the pulse, namely, the frequency of the acoustic wave. A second parameter is the magnitude of the acoustic wave, also termed the amplitude, as represented by the peak-to-peak value of the sound wave. Another characteristic is the angle at which the sound wave is directed towards the object under study. There may be other characteristic parameters which may also be varied according to principles of the present invention; the three being provided are examples of suitable parameters to achieved an improved holographic image as explained in more detail herein.

In one embodiment, the present invention provides an improvement to the device and process of ultrasonic holography imaging, especially in imaging for tumor masses in soft tissue. Each incremental improvement to either the apparatus or process or both, provided herein is able to increase holographic image quality. Therefore, the claimed invention is directed to each incremental improvement alone or to any combination with other incremental improvements in the ultrasonic holographic imaging process and apparatus.

BRIEF DESCRIPTION OF THE SEVERAL VIEWS OF THE DRAWING(S)

FIGS. 6A and 6B illustrate a further alternative embodiment for varying a characteristic parameter of the acoustic pulse according to principles of the present invention.

DETAILED DESCRIPTION OF THE INVENTION

Figure 1:
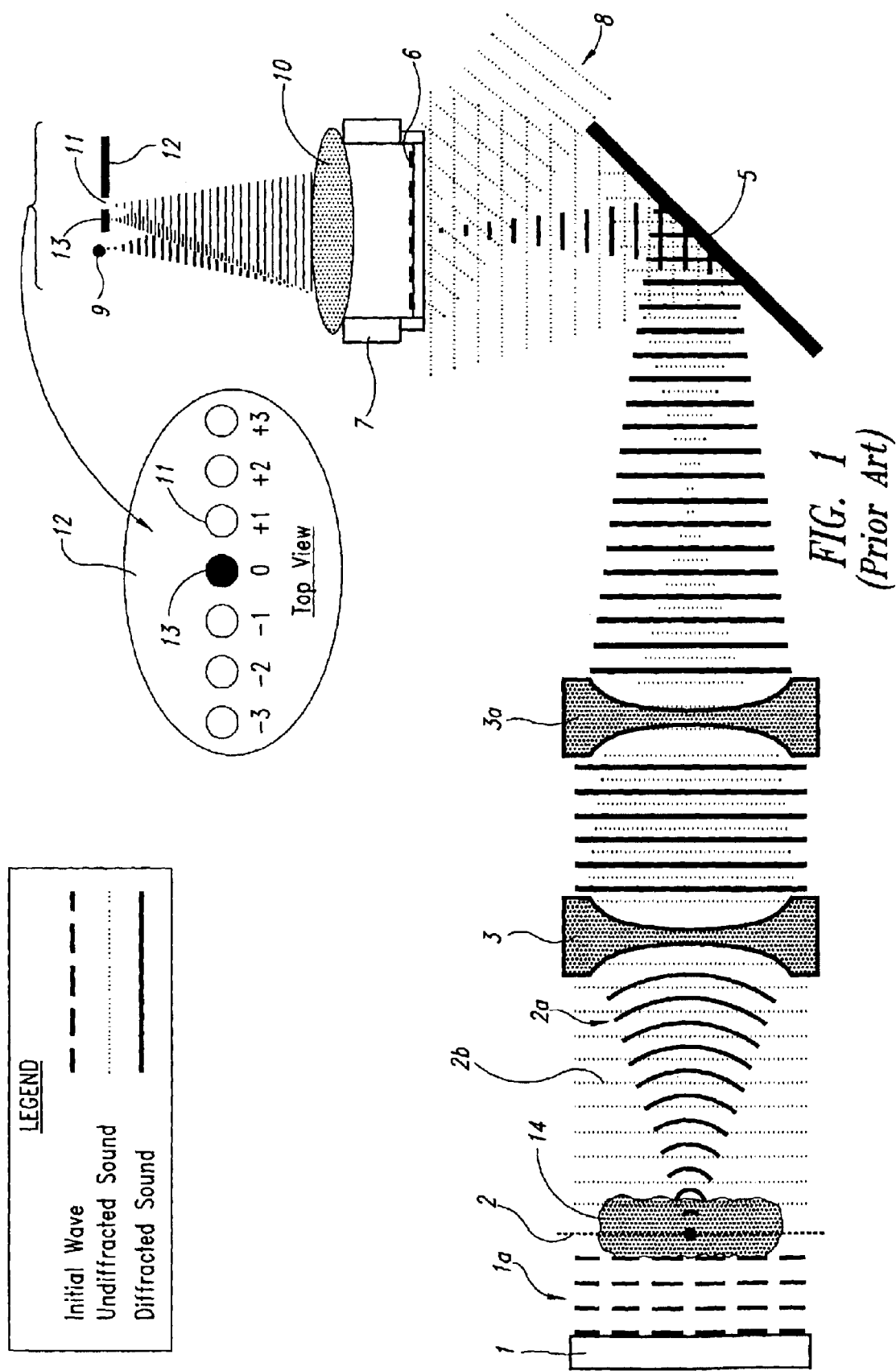
FIG. 1 is a pictographic representation of acoustical holography of an acoustic holographic system according to the prior art.

FIG. 1 illustrates an acoustic holographic imaging system according to prior art U.S. Pat. No. 5,329,817, incorporated herein by reference. This U.S. patent is owned by the same assignee as the present invention and shares a common inventor. A transducer 1 outputs an initial wave 1*a* which is transmitted towards the object 14 under study. Of course, the wave 1a can be any acceptable sine wave shape, such as a plane wave, a concave wave, a convex wave, or other acceptable shape. The sound enters the object 14 under study and preferably passes completely through the object 14. This type of hologram is termed a "through transmission hologram." The present invention is particularly advantageous with through transmission holograms though, of course, certain principles herein may also be applied to reflective holograms or other acoustic imaging techniques. A lens system 3 and 3a receives a sound wave 2a which has passed through the object 14. The sound that is diffracted from structures in the focal plane 2 within the object 14 based on the location of the lenses 3 and 3a relative to each other and to the object 14 under study. Of course, the lenses 3 and 3a can be moved in order to vary the plane 2 within the object under study in order to examine other portions.

The object under study emits two types of waves, scattered sound 2a and unscattered sound 2b. The acoustic wave passes through the lens system 3 and 3a and is transmitted to the acoustic reflector 5. The sound is then focused to a detector 6 having a side wall 7 and a lens 10 structured according to principles well known in the art. An off-axis reference wave 8 is also impinged upon the detector in order to form an acoustic hologram within the detector 6. A light source 9 beams light through the lens 10 which is reflected from the detector surface 6 to a sensing plane 12. The sensing plane 12 contains a number of apertures which can be either opened or closed depending on the desired image. The output acoustic wave includes a zero order diffraction 13, and other related orders of diffraction, such as a +1, +2, and +3 orders of diffraction and corresponding −1, −2, and −3 orders of diffraction. In some embodiments, in order to properly sense the acoustic hologram it is desired to block the zero order diffraction 13 with a blocking number 13 and receive the first order diffraction through an open aperture 11 as shown in FIG. 1. Other orders of diffraction as represented in the plate 12 can either be received or blocked depending on the desired image construction, the techniques of which are well-known in the prior art and are not described in detail herein.

Figure 2:
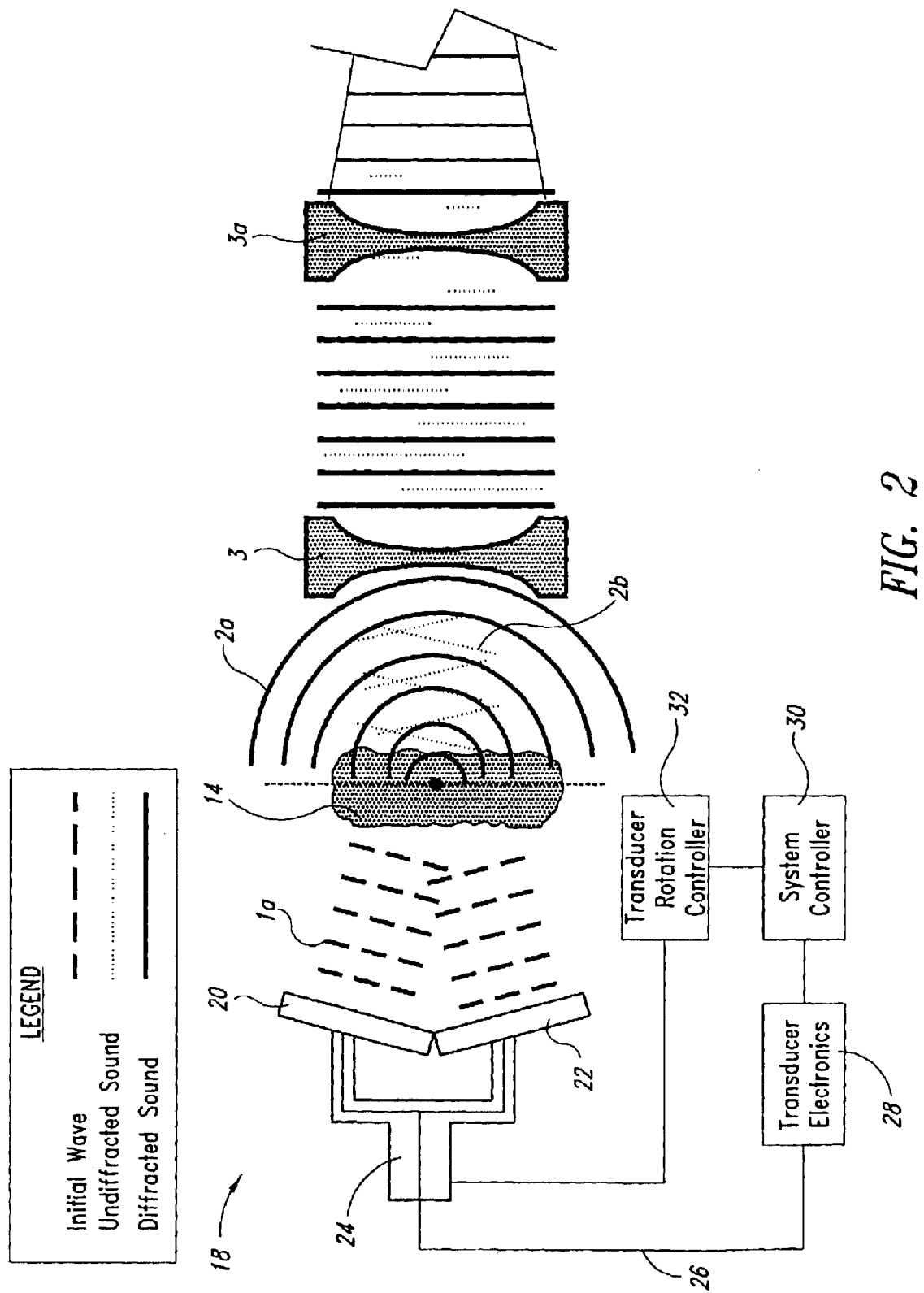
FIG. 2 is a pictographic representation of an acoustical holographic system according to principles of the present invention.

FIG. 2 illustrates one embodiment of an acoustic hologram according to principles of the present invention. The system for sensing the created hologram is the same as the prior art having a reflector 5, a detector plane 6 within a detector apparatus 7, a lens 10, and a plate 12. Therefore, these are not shown in FIG. 2.

As shown in FIG. 2, a transducer assembly 18 includes a first transducer 20 and a second transducer 22 coupled to a rotatable shaft 24. The transducers are connected by the appropriate electrical connections 26 to transducer electronics 28 which drive the transducers according to principles of the present invention as explained herein. A system controller 30 which includes a microprocessor and programmable software control is coupled to the transducer electronics 28 to send signals thereto and receive signals therefrom in order to provide control of the entire system. In one embodiment, a transducer rotation controller 32 is also provided coupled to the system controller 30. In an alternative embodiment, the transducers do not rotate or, alternatively, are not coupled to the system controller 30 but rather rotate independent. In one embodiment, the transducer rotation controller 32 is coupled to the system controller 30 which is able to rotate the shaft 24 and thus the transducers 20 and 22 in a desired synchronism with the transducers being driven by the transducer electronics 28. The system controller 30 therefore controls both the transducers 20 and 22 as well as the rotation of the transducers so that the output of pulses by the transducers can be selectively timed based on the rotational position of the transducers and their relative angle to the object under study.

Any acceptable transducer arrangement may be used. In one embodiment, the transducers 20 and 22 are at a selected angle relative to the object 14 under study. In another embodiment, three transducers are used rather than two, one transducer being a central transducer which is stationary relative to the object or may be mounted on a central location on the shaft 24 so that it has an offset angle of zero. This can be used as the sole transducer, or in combination with two other transducers 20 and 22 so that three transducers are provided for creating sound waves to image the object 14.

The present invention relates to the driving of the transducers in order to produce a desired holographic image as will now be described and as shown in FIGS. 3–9. In some embodiments, the invention also includes rotation of the transducers while pulses are being generated as explained and illustrated in more detail herein.

Figure 3:
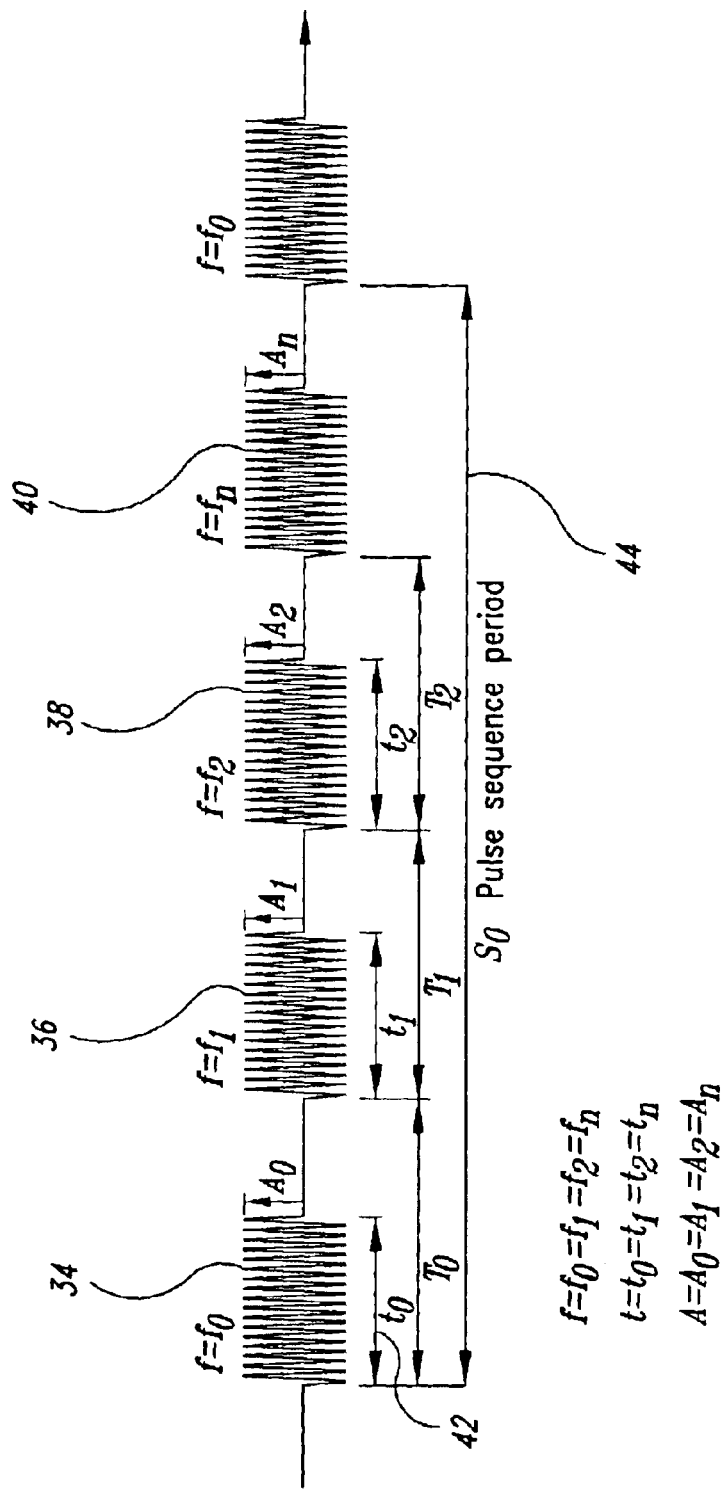
FIG. 3 illustrates pulses generated by the acoustic holographic system according to principles of the present invention.

FIG. 3 illustrates a plurality of pulses per sequence according to principles of the present invention. An acoustic pulse 34 is preferably in the form of the sine wave. The sine wave is a coherent sound source and is composed of a sufficient number of cycles to provide an image in the detector 6. The pulse 34, as with the other pulses 36, 38 and 40 has a number of properties, which may also be called characteristic parameters. One characteristic parameter is the frequency, $f_0$ for pulse 34. This is the frequency of the sound pulse. The frequency, in one embodiment is approximately 2 MHz. Other of the sound waves may be different frequencies, such as 5 MHz, 8, 10 or 12 MHz depending on the system. Another characteristic of the pulse 34 is the pulse length $t_0$. This pulse length 42 is the total time that the pulse is generated. Another characteristic parameter is the amplitude $A_0$ of the pulse 34. This is the intensity of the pulse and is measured by the swing from peak to peak of the sine wave making up the pulse 34. Yet another characteristic parameter of the pulse 34 is the angle θ at which it is passed through the object 14 under study. This parameter θ can more easily be seen in FIGS. 8 and 9 and will be explained in more detail with respect to such figures.

The pulse 34 is one pulse in a sequence 44 of the pulses. The pulse sequence $S_0$ is composed of a plurality of individual pulses 34, 36, 38 and 40. In one embodiment, there are four pulses in a sequence while in other embodiments, there may be fewer, such as three pulses per sequences while in other embodiments there may be more pulses per sequence, such as five or six. Each pulse in the sequence is separated by a period T. From the start of the first pulse to the start of the second pulse is the pulse repetition $T_0$ as shown in FIG. 3.

Each pulse 34 is defined by a number of characteristic parameters beyond those just described and the varying of different parameters may be appropriate in some applications. These particular characteristic parameters in the context of the production of holograms has particular significance. Within a single pulse 34, the characteristic parameters do not change. Namely, the frequency amplitude and angle along with other characteristics remain generally constant throughout the pulse. The pulses are relatively short, compared to the distance between pulses, the drawing in FIG. 3 not being to scale. For example, the pulse on time $t_0$ may be approximately 80 microseconds and the pulses are provided at a rate of 120 pulses per second. Accordingly, the $t_0$ for pulse 34 will be several sine waves followed by a quiet time during which the detector completes the sensing operation and returns to quiescent state to prepare for the next pulse which comes at the end of the pulse repetition $t_0$. Each individual pulse creates an hologram in the holographic detector the image of which is sensed and recorded as appropriate, whether with a CCD, still frame camera, or other recording instrument. According to one embodiment of the present invention, a separate image is made for each of the pulses 34, 36, 38, 40 and every other individual pulse so that 120 images per second are generated for review by the physician. Of course, different pulse on times $t_0$ as well as different pulse repetition periods $T_0$ may be used depending on system design and selections available.

According to one preferred embodiment, the image detector includes a CCD camera of a type well known in the prior art. Such a CCD camera has the capability to integrate a number of pulses into a single image and output a composite picture of the results of each of the pulses. The present invention is particularly advantageous with such a CCD imager. A number of shortcomings of prior art holographic images are overcome using the principles of the present invention which use a detector having a CCD imager as explained herein.

According to one embodiment, all pulses within a pulse sequence period 44 are integrated into a single image. Namely, the image created by each of the individual pulses 34, 36, 38 and 40 are combined and integrated into a single image which is output by a CCD detector for viewing. The CCD detector may output images of the entire sequence with all pulses combined as still frames or, alternatively may output the meta rate suitable for viewing on a video monitor. If the pulses are provided at 120 pulses per second and a pulse sequence is composed of four pulses then a new sequence is produced 30 times per second, which matches the scan rate of standard video monitors. Accordingly, the image created by the pulse sequence $S_0$ can be output to a standard video monitor and displayed using current technology with horizontal scan lines and fly back in between images as is well known in the art of video monitors. A new sequence 44 is created for each set of four pulses so the continuous images are provided to the video monitor of the acoustic hologram so that live viewing of the object is permitted.

FIG. 3 illustrates that three of the characteristic parameters of a pulse can be maintained the same from one pulse to another within the sequence. Namely, the frequency f is kept the same for each of the pulses such that $f=f_0=f_1=f_2=f_n$ as shown in FIG. 3. Further, the pulse on time t can also be maintained the same such that $t=t_0=t_1=t_2=t_n$. The amplitude can also be maintained the same so that the amplitude A is the same for each pulse namely, $A=A_0=A_1=A_2=A_n$.

Figure 4:
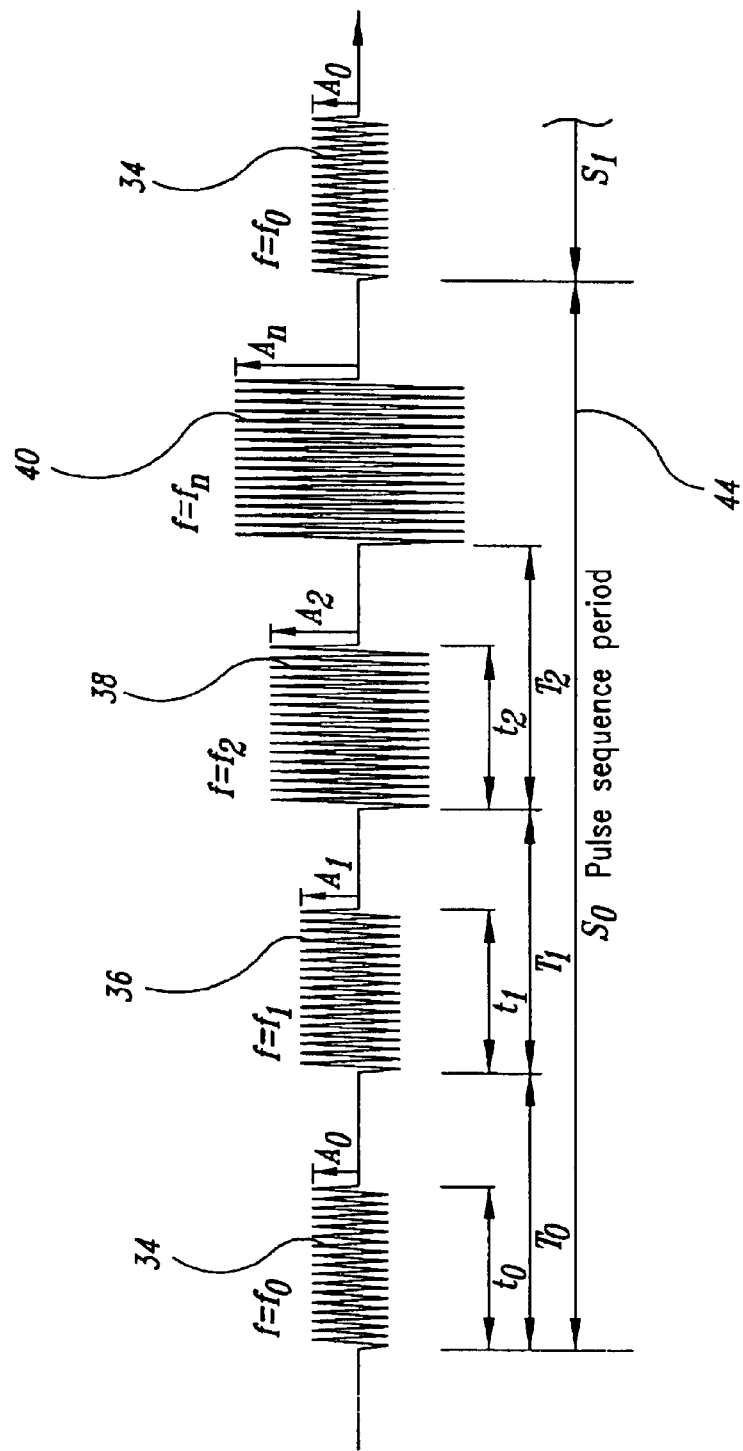
FIG. 4 illustrates one embodiment for varying a characteristic parameter of the acoustic pulse.

FIG. 4 illustrates varying one of these characteristic parameters from one pulse to another within the sequence. In particular, within the sequence $S_0$ the amplitude A is varied from one pulse to another. The first pulse 34 has an amplitude $A_0$. The second pulse 36 has an amplitude $A_1$ which is greater than $A_0$. The third pulse has an amplitude $A_2$ which is greater than $A_1$. Additional pulses within the sequence may have a different amplitude $A_n$. Accordingly, at least one characteristic parameter in this case the amplitude is different for different pulses. Two or more pulses may have the same amplitude $A_0$ while at least one pulse in the sequence has a different amplitude than other pulses in the sequence.

The actual pulses which compose a sequence may shift depending on the electronics and the timing. For example, the first pulse in the image being generated may be shifted somewhat from the first pulse 34 in the electronic sequence as generated and it is not necessary that the detector be synchronized with the pulse generator in order to ensure proper operation. Accordingly, the detector will create a single image from a sequence which is not an exact match to the sequences generated at the transducer. For example, the pulse sequence generated at the detector may include the last two pulses of one sequence and the first two pulses of another sequence as generated in the transducer. In a preferred embodiment, the number of pulses within a sequence generated at the transducer is the same number of pulses which are incorporated into a single image by the detector. Accordingly, if the images created by the detector is shifted to start at different pulses within the generated sequence the image will still be unchanged since one pulse of each of the types of pulses within a single sequence are received by the detector even though the order in which they are received may differ slightly. According to an alternative embodiment, the number of pulses within a sequence as generated by the transducer may be different from the number of pulses into a single image as incorporated by the detector. For example, the pulse sequence as generated by the transducer may include 5, 6 or more pulses whereas the number of pulses incorporated into a single image by the detector may include a sequence having 3, 4 or a different number of pulses. In the event the transducer and detector electronics are improved such that pulses are generated at 240 per second or at a higher rate and the detector creates individual images at this rate, namely the same rate at which the pulses are generated it may still be desirable to integrate into a single image the correct number of pulses in order to create one new image 30 times per second for matching with a standard TV monitor. In this instance, there may be 8 pulses per sequence and also 8 pulses in the image per sequence so that there remains a match between the number of pulses in each sequences generated remains a match and is exactly the same number of pulses in each image as created, which is preferred. Alternatively, it is possible with the present invention to have a different number of sequences within the image as created than in the pulse sequence as generated by the transducer in order to highlight certain attributes of the tissue if desired.

Figure 5A:
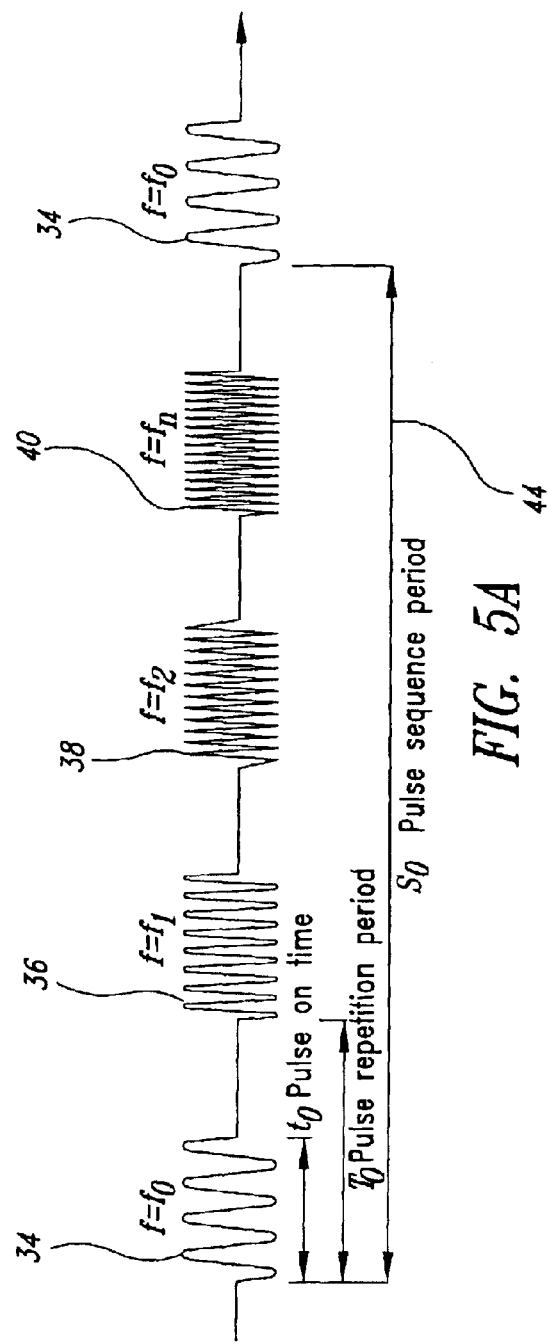
FIGS. 5A and 5B illustrate additional examples of varying a characteristic parameter of the acoustic pulse according to principles of the present invention.
Figure 5B:
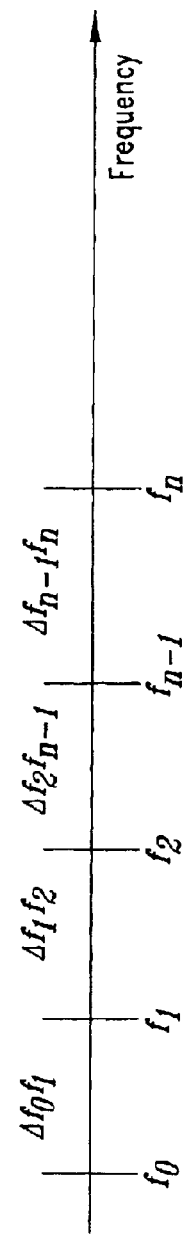

FIGS. 5A and 5B illustrate another characteristic parameter, namely the frequency being changed for different pulses within the same sequence. For a given sequence 44 the frequency f is different for different pulses within the same sequence. The first pulse 34 has a first frequency $f_0$ whereas the second pulse 36 has a different frequency $f_1$. Other pulses within the same sequence will have different frequencies. According to one embodiment of the present invention as shown in FIG. 5B the difference from one pulse to another is a constant. Namely, the difference in frequency from the first pulse to the second pulse is the same as the difference in frequency from the second pulse to the third pulse. Thus, as shown in FIG. 5B, $\Delta F$ between pulses is a constant. As one example, the first frequency may be at 2 MHz, the second frequency 4 MHz, the third frequency at 6 MHz and the next frequency at 8 MHz. Thus, the difference from one frequency to another is a constant number. Alternatively, it may be desirable to double the frequency from one frequency to another. For example, the first frequency being 2 MHz, the second 4 MHz, the third 8 MHz and the next 16 MHz. In this case, the difference between one frequency and another is a doubling from the prior frequency, however the $\Delta$ change is a constant, preset value based on a beginning frequency.

FIGS. 6A and 6B illustrate a further alternative embodiment for changing the characteristic parameter of the frequency. As can be seen in FIG. 6A, the difference in frequency from the first pulse 34 to the second pulse 36 can be relative small, so that the frequencies of the first and second pulses are relatively close to each other as shown in FIG. 6B. A third pulse 38 can have a frequency $f_2$ that is a difference which is nonlinear from the difference between the first two pulses. For example, the frequency of the third pulse 38 is selected to achieve certain imaging characteristics without regard to the frequency of the prior pulses. In this instance, the frequency of each pulse is individually selected to provide a contribution to the final image which is composed of all pulses in the sequence. The selection is done with a goal of providing and viewing of individual characteristics within the object under interest which may be better viewed at selected frequencies. Additional frequencies may also be included within the sequence, the frequencies being selected based on a desired characteristic to be viewed within the object or, in order to obtain an incredibly high frequency. For example, one frequency $f_n$ can be a very high frequency in order to attempt to image certain aspects within the object under study. This frequency can be spaced from other frequencies if desired or can have one or two other pulses of similar frequencies adjacent to it. In this instance, the difference in frequency from one pulse to another within the same sequence is not uniform. Of course, as with the other embodiments two or more of the pulses may be of the same frequency as each other while additional frequencies within the same sequence may be different from the other two.

Figure 7:
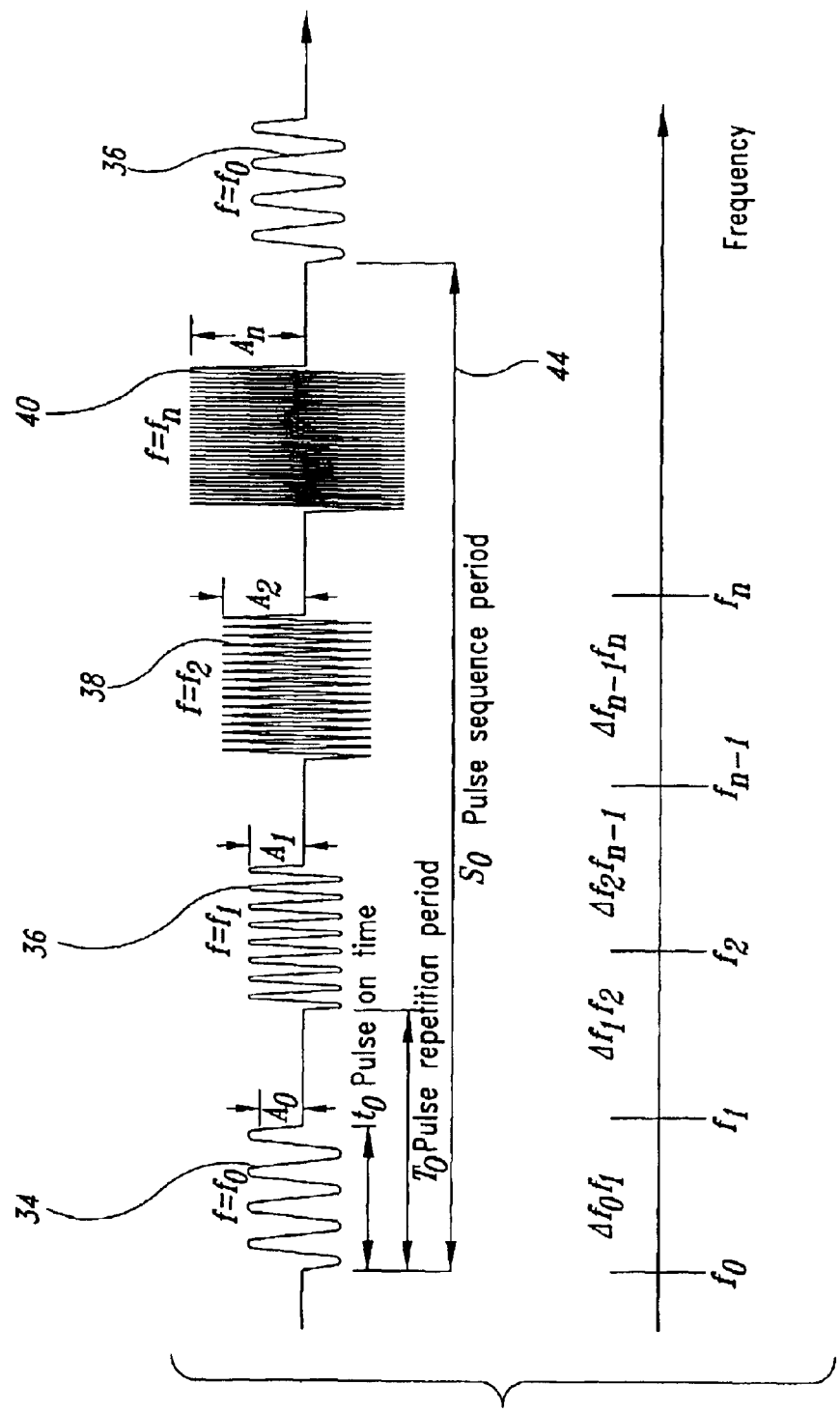
FIG. 7 illustrates varying a plurality of acoustic parameters from pulse-to-pulse according to principles of the present invention.

FIG. 7 illustrates a preferred embodiment of the present invention which takes advantage of generating a holographic image using a CCD imager to create one image per sequence 44. According to the embodiment of FIG. 7, two characteristic parameters, the frequency and the amplitude are changed from one signal to another within a single sequence. The higher the frequency the more it is attenuated as it passes through an object under study. For acoustic waves, a low frequency sound wave has a greater amplitude after passing through an object than a higher frequency has after passing through the same object. As a general rule, a given object usually provides greater attenuation of higher frequency sound waves as the acoustic waves passes through the object. If an image is being created from a sequence of pulses at different frequencies this creates the disadvantage that frequencies at higher pulses have a lower intensity as received at the detector and their contribution to the image will be less. One way to correct the difference in intensity as perceived by the detector is to increase the amplitude of the signal in proportion to the loss associated with the change in frequency. Namely, as the frequency increases from the first pulse to the second pulse the amplitude of the second pulse is also increased in an amount corresponding to that needed to have the acoustic pulses arriving in the detector be of the same amplitude. For some acoustic waves, the change in amplitude from frequency to frequency, depending on the object may be somewhat linear over certain frequency ranges. On the other hand, as the frequency gets higher the effects of attenuation may be increased so that a direct linear expansion of the amplitude may not be sufficient. In a preferred embodiment, the amplitude of the pulse is selected based on the frequency so that the received amplitude at the detector is the same for each pulse for its respective frequency. In some embodiments, the amplitude increase will correspond proportionally to the frequency increase while in other embodiments, additional adjustments in amplitude may be needed. For example a greater amplitude increase may be needed at some of the higher frequencies than a proportional increase. The amount of amplitude required can easily be determined by sensing at the detector the amplitude of the received signal and calibrating the amplitude needed for the acoustic wave as generated that will provide the desired amplitude of the output wave as detected. This can be determined empirically by simple calibration tests and then preset into the equipment at the time of manufacture. Other calibrations may also be provided in order to calibrate a desired frequency within the sequence whether the change from one frequency to another is constant or whether it will be variable at selected intervals as shown in FIG. 6. Each of these calibrations can be stored in the memory within the system controller so that as the device is operated in different modes of operation such as illustrated in FIGS. 3–7 that the transducers are driven as appropriate to achieved the correct final image at the detector.

The present invention therefore has the advantage of providing an automatically corrected final image at the detector based on the pulse sequences as generated at the transducer. The relative weighting of each pulse is selected so as to provide the desired contribution to the final image. Generally, it will be desired that each pulse will have an equal contribution to the image and accordingly, the amplitude will be selected for each pulse as generated so that the amplitude of each pulse as received at the detector will be the same. The image created from such a sequence will therefore have an equal contribution from each pulse. Alternatively, it may be desired to provide a stronger component to the higher frequencies in which case, the amplitude of such frequencies as generated at the transducers will be increased beyond the proportional amount and the pulse corresponding to that frequency will be given a correspondingly greater weight in the final image created of the sequence.

Figure 8:
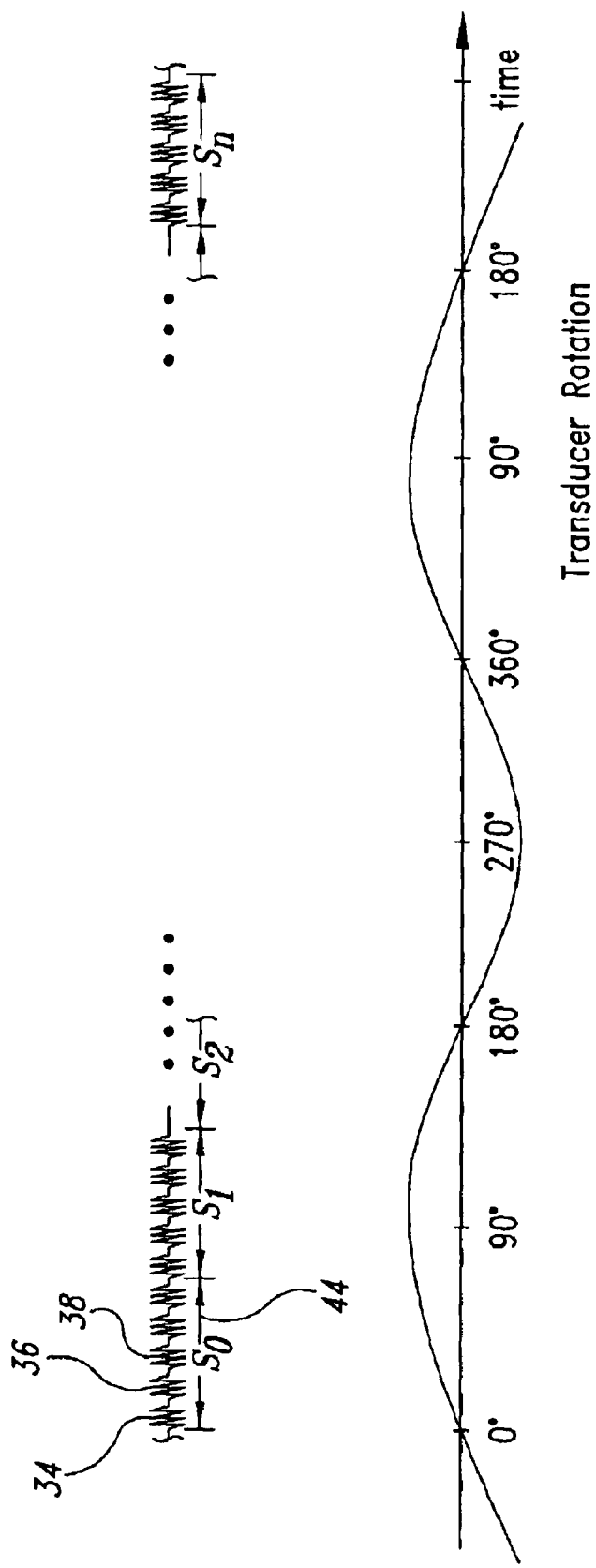
FIG. 8 illustrates varying an additional acoustic parameter according to principles of the present invention.

FIG. 8 illustrates another characteristic parameter which may be modified according to principles of the present invention. One of the characteristic parameters of an acoustic holographic beam is the angle at which it is generated for entry into the object under study. A plane wave produced by a single transducer as shown in FIG. 1 enters the object at 0° for each pulse. The angle orientation does not change from pulse to pulse and is a straight through wave. Depending on the object under study, it may be desirable to view some portions at a different angle so as to highlight selected images. For example, blood vessels, lymph nodes and other portions of the human anatomy are more distinctly imaged with ultrasound that is at a different angle than straight on. For such imaging, having the transducer offset with respect to a center axis or, advantageously rotating the transducer provides increased sensitivity to the other features in the object under study. FIG. 2 illustrates an example of two transducers at different angles to the object under study. In one embodiment, the transducers remain stationary so that all images are at a preset angle of the acoustic wave passing through the object under study. In this case, a number of images are created which correspond to the view of that object at the selected angle. In FIG. 2, this angle is shown as about 8°, but other angles can be selected. As an alternative, the transducer may be rotated using rotation controller 32 as illustrated in FIG. 2. The transducers can be rotated using the appropriate motors at a speed which is acceptable for the object under study. According to one embodiment, the speed of rotation may be sixty revolutions per minute while in other embodiments, it may 100 or 120 revolutions per minute. Of course, the transducers may also be moved quite slowly, such as 2 revolutions per minute if desired. If the transducers are rotated at 120 revolutions per minute then this corresponds to 2 revolutions per second or, 1 revolution for every half second. FIG. 8 shows one full revolution from 0° to 360° of the transducer shaft 24. The angle remains constant, but the relative orientation is varied as the shaft rotates If a transducer pulse rate of 120 pulses per second is selected then 60 pulses are generated each full revolution which corresponds to 15 sequences per revolution if there are four pulses per sequence. FIG. 8 illustrates a number of sequences 44 being generated for each rotation of the transducer, but not to scale.

According to one embodiment, the transducers are rotated under control of the motors drive in the shaft 24 at desired rate independent of the timing of the pulses being sent to the transducers. This will have the effect of creating a random pattern of the sequences at various orientations throughout the transducer rotation. Different images will be created at various orientations based on the interaction between the rotation of the transducers and the timing of the pulses generated by the transducer electronics. The angle may also be varied, as described in U.S. Pat. No. 5,329,817.

In some embodiments, it is preferred to collect the data with the transducer rotation not synchronized to the transducer electronics so that the images have a form of randomness in the sequence orientation with respect to the object for each image. Thus, some images may be generated in the first quarter of the rotational cycle while other images are created in the second quarter of the cycle slightly offset. As shown in FIG. 8A, for example the sequence 44 may include 5 pulses as generated by the transducer electronics 28 and 4 pulses in the detector thus creating an established offset which has some randomness with respect to the orientation of the transducers for each image created.

Figure 9:
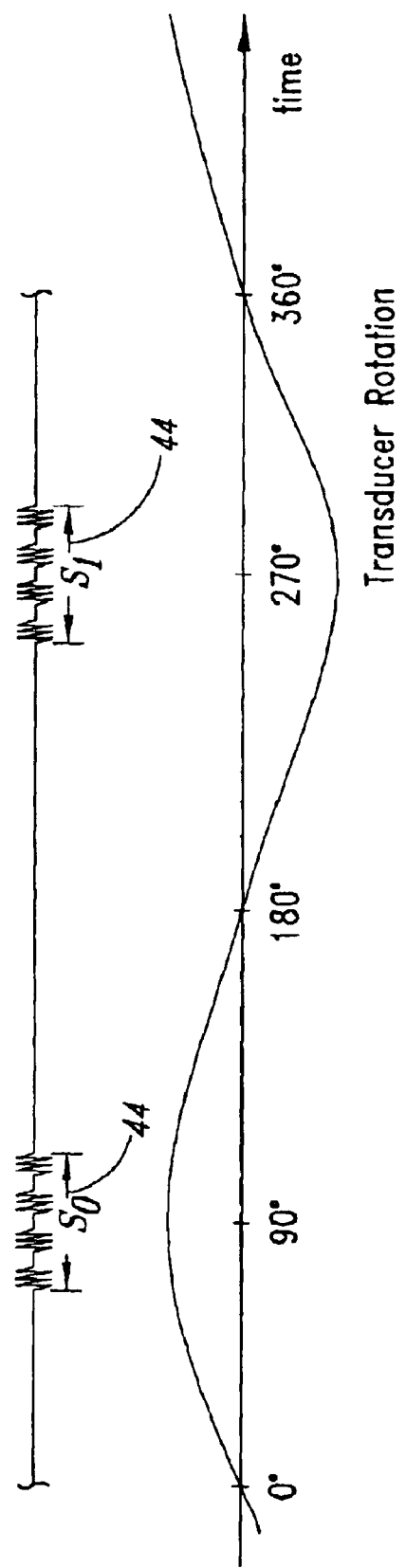
FIG. 9 illustrates another alternative embodiment of varying an acoustic parameter according to principles of the present invention.

FIG. 9 illustrates an alternative embodiment in which the transducer rotation is synchronized to the pulse generation. In this embodiment, the system controller provides a synchronization between the transducer rotation controller 32 and the transducer electronics 28. In the example shown as FIG. 9, a selection has been made to generate each sequence at a selected orientation and angle with respect to the object. The angle of propagation can be selected to achieve a view in the image that causes certain features in the object to be more prominate. For example, the images can be created by sound at a selected angle such that the path of propagation is perpendicular to linear structures in the object to make from them more visible. In the example of FIG. 9, the sequence of pulses is generated at about the 90° and 270° location in each revolution of the transducers 20 and 22. At other positions, no pulses are generated, for example, as the rotation of the transducer passes through the zero crossing point at 0° and 180° no pulses are sent so that the images which are created do not have any contribution from these particular positions and angles of orientation of the transducer.

In the embodiment of FIG. 2, the transducers 20 and 22 are equally offset with respect to each other around the central axis 24 and further, always have some offset relative to the object. This is preferred in some embodiments. As an alternative embodiment it is desirable to have a single transducer with an offset, which offset may change based on the rotational characteristics of the shaft 24 or the angles of movement. A number of the transducer rotational and angle characteristics are described in detail in U.S. Pat. No. 5,329,817 which is incorporated herein by reference. For example, FIGS. 7, 8 and 9 of this issued U.S. patent, as well as FIGS. 12 and 13 illustrate different embodiments for moving a transducer relative to an object while acoustic waves are being generated for passing through the object. The transducer rotation can be mapped as shown in FIG. 9 as having a selected action. FIG. 9 illustrates circular motion of the transducer through 360°. Of course, other motions may also be used as explained in the '817 patent. These motions can be synched to the generation of acoustic pulses by the transducer electronics so as to achieve a desired angle of orientation for each sequence of pulses through the object for generation of images of the detector. Thus, as illustrated in FIGS. 8 and 9 a further characteristic parameter of the sequence 44 of acoustic waves is the angle of orientation at which it is transmitted through the object. It may be desired, in some embodiments to change only the angle of orientation from image to image as the characteristic parameter to be changed. Alternatively, other of the characteristic parameters discussed herein such as frequency, amplitude, pulse on time $T_0$, the number of pulses in a sequence $S_0$ and other parameters may also be changed in order to achieve an enhanced image of particular characteristics of the object under study.

Figure 10:
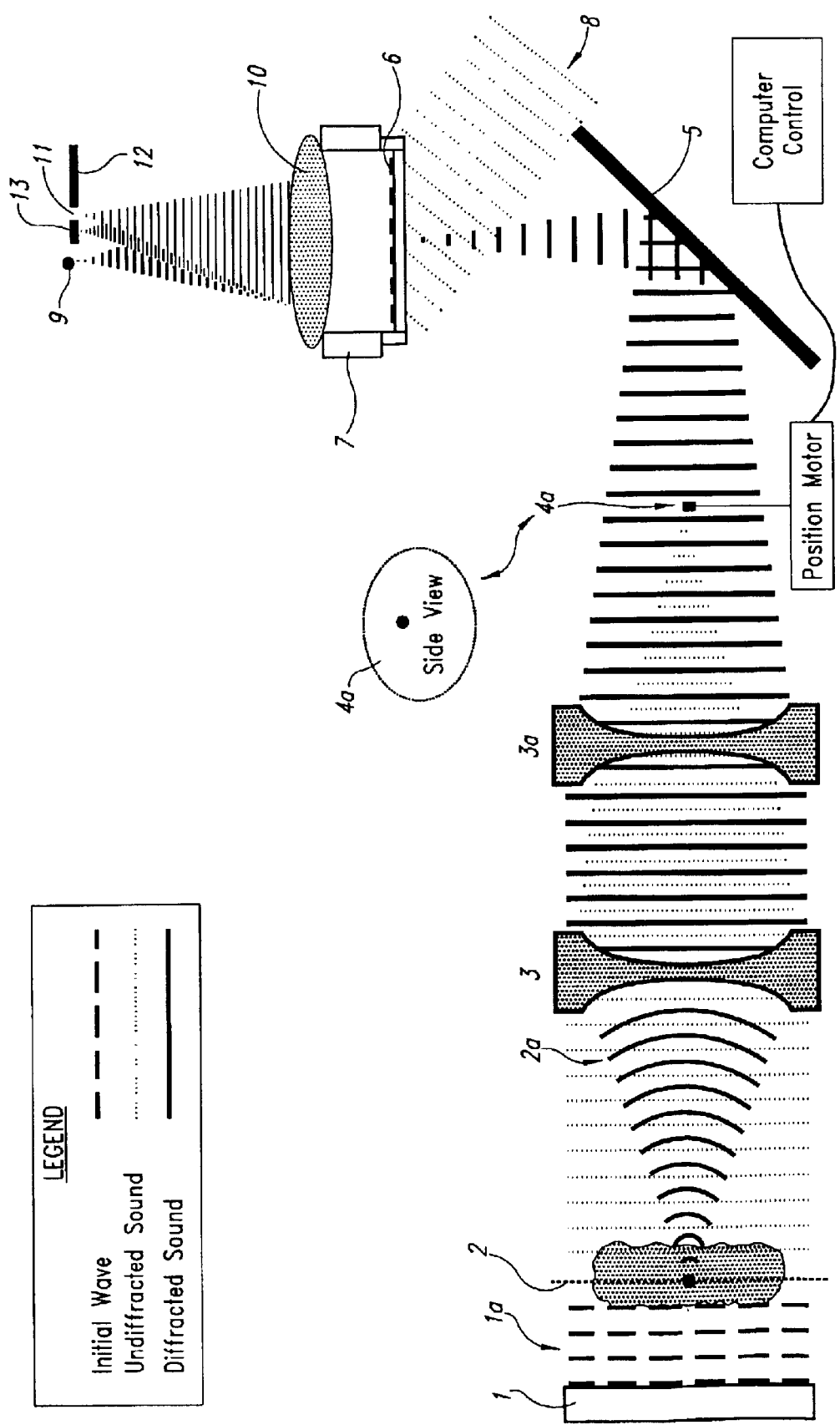
FIG. 10 illustrates a pictographical representation of an apparatus for varying the background according to principles of the present invention.
Figure 11:
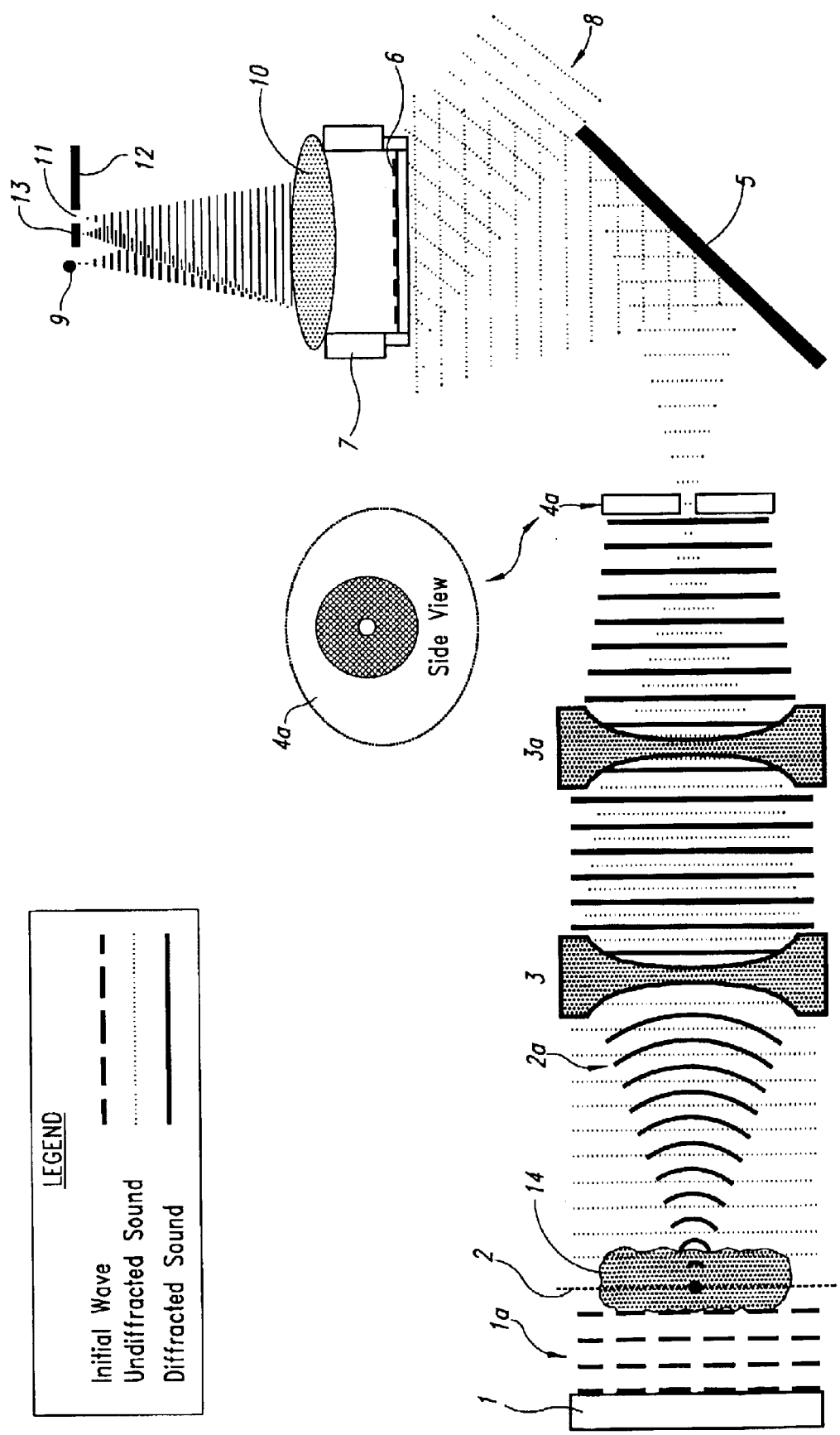
FIG. 11 illustrates an alternative embodiment for varying the background according to principles of the present invention.

FIGS. 10 and 11 illustrate a further improvement in accordance with one embodiment of the present invention. According to his embodiment, a sound blocking member 4a is positioned at a selected location within the acoustic wave in order to block a desired type of sound. In the embodiment of FIG. 10, an acoustically opaque element 4 is placed at the focal point of unscattered sound. This results in forming a hologram with scattered sound only which causes a light image on a dark background. This may also be termed as "dark background imaging." The acoustic opaque element 4a is movable to various locations by a position motor 57 under control of a computer controller 59. Of course, the computer controller 59 can be the same controller as the system controller 30 in some embodiments or, alternatively, can be a separate computer controller.

FIG. 11 illustrates an embodiment in which the acoustic blocking member 4a is a planar acoustic element with an opening positioned at the focal point of and passing unscattered sound while blocking sound scattered by the object, thus forming a dark image on a light background. Accordingly, an acoustic opaque element 4a can be incorporated together with other features of the present invention in order to provide an enhanced image at the detected plane 12. The subject matter of the acoustically opaque element is described in more detail in U.S. patent application Ser. No. 09/590,148 and U.S. patent application Ser. No. 09/982,209, both of which are incorporated herein by reference in their entirety.

The control program for operating the system can be provided in the system control electronics as the equipment is manufactured. Accordingly, the features will be enabled based on the hardware configuration of the machine as supplied by the manufacturer. In one alternative embodiment, the hardware as provided to the user has a number of user-selectable options which have been previously provided as stored in the control system memory. The user may select an option to vary the frequency as shown and described herein with respect to FIGS. 5A, 5B, or according to FIGS. 6A and 6B. The user may also programmably select an option to vary the amplitude according to FIG. 4. Alternatively, the user may select the option to vary the frequency and the amplitude as described and shown with respect to FIG. 7. According to one embodiment, the machine system control is largely software programmable to achieve all of these characteristics and provide user programmability. In particular, the system controller is interfaced with a computer, or itself is a computer. The computer has software codes stored in the memory in the form of operational instructions for the acoustical holographic device. A user may program the system in order to vary any desired characteristic parameter of the sound wave for each pulse so as to create a sequence of pulses having the desired characteristics. Thus, an image can be custom-formed by the user selectively generating those pulses within the sequence in order to enhance those properties which are desired to be viewed. Depending upon the object under investigation, such as human tissue being investigated for cancer, it may be desirable to vary a number of the operational characteristic parameters described herein at the same time while leaving other parameters constant, so as to selectively enhance that portion of the tissue which is being examined. For other tissue, the operation is programmable to vary a completely different set of characteristic parameters so the images from a different aspect of the same tissue, or different tissue, can be generated having particular features more prominently viewable within the displayed final image. The present invention is therefore sufficiently flexible that in one embodiment the user is able to selectively build a custom set of pulses for each sequence, so that an image is created having the desired features displayed with the attributes so as to enhance the medical value of such an acoustic hologram and remove unwanted artifacts.

In general, the present invention provides a process and an apparatus for generating multiple exposure ultrasonic holography images generated from a specific selected orientation each of which will permit multiple images, multiple intensities or multiple frequencies from each orientation. The process and the apparatus is designed for providing a multiple view, multiple angle insonification of the object such that the object sound intensity is of equal or near equal intensity across the entire field of the object. The process and the apparatus provide individual images at specific views and at specific intensities and frequency of sound to compare and analyze to achieve increased diagnostic value of the imaging process.

The present invention provides for multiple views of an object to be imaged with each view forming a separate hologram. Each separate hologram is constructed independently and at a rate (can be greater than 120 Hz) that is greater than the motion detection of the human eye (assumed to be approximately 30 Hz) and a rate required by a data acquisition apparatus (e.g., standard frame rate of CCD cameras). Thus, an averaging of "out of focus" contribution to the image is achieved to enhance the focusing capability of the acoustical holography process. There is an opportunity to have multiple of images that get collected into one composite image for viewing. This can be thought of in a similar manner as frame averaging but is different in that multiple images are combined into each "frame" of the output device. These multiple images then can be taken at multiple angular views to minimize the effect of "out of focal plane" structures. This process is the basis of U.S. Pat. No. 5,329,817 that provides an apparatus for multiple view images by either rotating the object transducer, making it "wobble" to achieve a multiple of off axis orientation, or by multiple pulsing individual transducers in a set array while the imaging process is underway.

The present invention provides a matrix of improvements to image quality, such as, providing for such "off axis" views to be electronically synched. From each selected view, one may arrange apparatus that will provide the final image to be made up of only those selected views rather than at random angles. This will allow an operator to pre-select the preferred views from which to best see the structures of interest in the object and discriminate against others. Further, the apparatus provides a different ultrasound frequency to be used at each separate orientation or view, thus taking full advantage of not only the preferred orientation but also to improve the imaging of the subtle nature of structures, such as, edges and frequency sensitive soft tissue structures (tumor masses). In addition, the inventive apparatus allows for individual images to be formed at various frequencies with electronic compensation such that each frequency contribution is "equalized" such that all frequencies make a equal image intensity contribution to the composite final image.

A further disclosure provided herein is an apparatus that will provide for a different ultrasound intensity to be used at each separate orientation thus taking full advantage of not only the preferred orientation but also to improve the diagnostic value of the imaging process by differentiating the transmission characteristics of the subtle nature of structures (including, for example, entrapped air, bone, and cancerous tissue that each have different sound absorption and transmission characteristics). The inventive apparatus comprises multiple transducers on a rotating head or an oscillating assembly that can be rotated in a continuous motion while selecting specific orientations in which to make the holographic view or may be stopped at a preferred orientation and changed slightly by the operator to optimize the resulting view of the structure of the object of interest. As an example, three transducers (more or less) are orientated at 0, +5 and −5 degrees from the central axis of the acoustic path. Each of the transducers is sequentially used to perform subsequent images. This multiple transducer head is rotated and the image sequences synched such that preferred views are selected or held at a single orientation, controlled by the operator. This allows the operator to adjust the orientation for an optimum view while selecting the frequencies and sound intensity to be used for greatest diagnostic value of the image from the selected view.

Still a further improvement to the inventive apparatus is an "off acoustic axis" viewing angle that is adjusted. Such an adjustment process is selected in conjunction with the selection of the f Number. Moreover, the lens sharpens or expands the width of the focal plane. Thus, the apparatus will insonify the entirety of the object (to be viewed, such as breast tissue) at an equal or near equal sound intensity. One can also insonify selected portions of the object with greater intensity (e.g., near the chest wall when imaging a human breast). It should be noted that in human breast imaging, defining the location of the chest wall for purposes of orientation is of importance to the diagnostic process, because this portion of the anatomy has the greatest thickness and requires a greater amount of sound intensity than other portions of the breast.

View Orientation

The view orientation of the object to be imaged is synched to achieve an enhanced image of greater clarity and quality. While U.S. Pat. No. 5,329,817 achieved a multiple view to provide improved imaging in a selected focal plane of the object, the selection was random. A random selection proved to seldom be the preferred orientation. In other words, U.S. Pat. No. 5,329,817 described a process of having a large number of images (e.g., 120 per second) over the time frame of observation by the human eye or frame collection time of the recording camera (e.g., 30 frames per second). This process combined or averaged random orientations within a circular or wobble position of the object transducer. Although this averaging provided enhanced focal plane identification, the image information in the focal plane seldom was optimum due to a random orientation.

The present invention, by contrast, continues to provide an advantage of enhanced focal plane definition through multiple orientations and multiple views, but adds the key feature of being able to achieve multiple views from a non-random orientation that best illuminates and identifies the structure being imaged. For example, if one is primarily interested in imaging a tubular structure (e.g., a vein within the human body or a ductile structure of the female breast), the most informative view is achieved from multiple views with angles of orientation from the center line of the acoustic lens being in a plane that is perpendicular to the primary axis of the tubular structure.

Enhanced Image Information

The present invention provides for an enhanced image information of subtle structures from multiple frequency and multiple intensity imaging at a selected orientation. Taking sequential images at different frequencies enhances the image information and clarity. For example, combining separate images, each taken within a small time interval (e.g., 1/120 of a second), and each taken sequentially at one of several selected frequencies will significantly sharpen edge definition and smooth the grainy appearance of an image made with a coherent wave. There is image improvement as the number of frequencies and the range of frequencies is increased. The reason for this improvement is primarily for two reasons. First, the nature of holography requires that the image be formed with a single coherent sound source. However, making images with such coherent waves makes the image appear grainy due to the self-interference of the coherent wave. Combining several images at different frequencies smoothes out the appearance of the image and smoothly present greater levels of intensity referred to as gray scale. Secondly, there is an increased definition of edges and boundaries. This improvement results from the same considerations of needing many frequencies to successfully describe a sharp step boundary with a mathematical series of sine waves.

Previously, the orientation of view was not synchronized with the timing of the pulse of sound from the rotating object transducer source. Accordingly, the location at which a given image was taken became random as to rotational angle around the axis of rotation. This resulted in having multiple frequency images being taken at unpredictable orientations. Thus, there could occur images at one rotational angle being highly concentrated at one or two frequencies and being absent of contributions from other frequencies being used. The advantage of multiple frequency imaging was to use all of the sequence of frequencies within the range for each composite image taken but randomness compromised this advantage. The inventive process, by contrast, provides for the monitoring of the angular rotational position of the rotating transducer or the angular position of a wobbling transducer arrangement. A wobbling transducer is defined as one that is rotated in one dimension around an axis that is parallel to one of the centerlines of one dimension of the transducer face. By monitoring the rotation or wobble position of the source transducer, one can then control the start time of the image sound pulse and achieve a controlled view as well as a controlled frequency or intensity sequence within the selected view.

Combining Images

Each image is taken at sequential frequencies and with adjusted acoustic amplitude for equal image contribution. There is improved image quality from separately analyzing or combining images at discrete and separate frequencies. However, there is also an attenuation of sound through most objects that depends upon the frequency of the sound being used. That is, the higher the frequency of the sound the greater attenuation through the object (e.g., human tissue). Thus, in the operation U.S. Pat. No. 5,329,817, images from the lower frequencies made a brighter contribution to the composite image than those at higher frequencies. Also since there is a sequence of frequencies, that are repeated, this unbalanced contribution of frequencies causes the image contribution to flicker at the repetition rate of the overall sequence.

The present invention provides an electronic means of adjusting the amplitude of each energy pulse depending upon the frequency value and thus the attenuation of the sound at that frequency. This equalization of image contributions for each frequency allows the image to be constructed from a composite of images each of which makes equal contribution to the composite image and thus optimizes the improved affects of a smooth appearing image and one with sharper edge definition.

In U.S. Pat. No. 5,329,817 a method and apparatus is described that allows for multiple views of an object with a single transducer, wherein each view forms a separate hologram. Since these holograms are constructed independently and at rates (can be greater than 120 Hz) that are greater than the motion detection of the human eye (approximately 30 Hz) and the rate required by data acquisition apparatus (e.g., standard frame rate of CCD cameras) an averaging of "out-of-focus" contribution to the image is achieved to enhance the focusing capability of the acoustical holography process. Thus, there is an opportunity to have multiple of images that get collected into one composite image for viewing. This can be thought of in a similar manner as frame averaging but is different in that multiple images are combined into each "frame" of the output device. These multiple images then can be taken at multiple angular views to minimize the effect of "out-of-focal plane" structures. Thus, U.S. Pat. No. 5,329,817 discloses an apparatus that will obtain multiple view images by either rotating a transducer, making a single transducer "wobble" to achieve a multiple of off-axis orientations, or using a multiple pulsing single transducer in a set order while the imaging process is underway.

Choice of Imaging Parameters

The present invention, essentially, provides a matrix of various variable parameters of ultrasonic pulsed wave transmission. The choice and selection of each of the multiple parameters depends entirely of the nature of the object to be imaged. For example, to image bone tissue in the presence of soft structure, a person skilled in this art will use a lower frequency (e.g., 1–2 MHz) and a higher amplitude because the lower frequency is less attenuated. Moreover, bone tissue has much greater attenuation than the surrounding soft tissue. Similarly, subtle soft tissue structures (e.g., tumor masses) will be more information if take at higher frequencies (e.g., 3–10 MHz) to show subtle structures of soft tissue. One skilled in the art will benefit by having the option of taking images at selected amplitudes and specifically selected frequencies to best achieve image information quality and information of the tissue at interest. Moreover, the ability to combine into one image, multiple images taken at different frequencies and amplitude provides greater image information than each separate image It should be noted that frequency and amplitude parameters can be adjusted during an imaging process, such as when an object to be studies in more detail is noticed. In such a situation, for example, the field can be enlarged or "zoomed" into the object to be studied and the frequency and amplitude adjusted to correspond to the optimal parameters of this newly enlarged field. For example, if bone tissue is present in a "wide angle" image, the frequency of a zoomed in image can be altered to account for the type of information to be obtained and the presence or absence of harder bone tissue within the zoomed image.

Amplitude, a used herein, refers to the intensity of the energy provided within a pulse wave of acoustic holography.

In summary, one aspect of the present invention is to allow off-axis views to be electronically "synched" such that from each selected view one may arrange apparatus that will provide the final image to be made up of only those selected views rather than at random angles. The many advantages provided include the ability of an operator to pre-select the preferred views from which to best see the internal structures of interest in the object and discriminate against others that might detract from the image.

The inventive apparatus enables a different ultrasonic energy to be used at each separate orientation. This provides a process to take full advantage of not only the preferred orientation but also to improve the imaging of the subtle nature of structures, such as edges and frequency sensitive soft tissue structures. This further allows individual images to be formed at various frequencies with electronic compensation such that each frequency contribution is "equalized" such that all frequency make a equal image intensity contribution to the composite final image. When a different ultrasound intensity is used at each separate orientation, the diagnostic value of the imaging process improves by differentiating the transmission characteristics of the subtle nature of structures e.g., entrapped air, bone, cancerous tissue which have different sound absorption and transmission characteristics.

The inventive apparatus provides for multiple transducers on a rotating head that are allowed to rotate in a continuous motion while selecting specific orientations in which to make the holographic view or are stopped at a preferred orientation and changed slightly by the operator to optimize the resulting view of the structure of the object of interest. For example, three (more or less) could be orientated at 0, +5 and −5 degrees from the central axis of the acoustic path. Each of the transducers are then sequentially used to perform subsequent images. This head is rotated and the image sequences synched such that preferred views are selected or are held at a single orientation, which is controlled by the operator. This allows the operator to adjust the orientation for an optimum view while selecting the frequencies and sound intensity to be used for greatest diagnostic value of the image from the selected view.

The inventive apparatus allows an "off acoustic axis" viewing angle to be adjusted. Such a process is selected in conjunction with the selection of the f Number of the lens to sharpen or expand the width of the focal plane. Moreover, the apparatus will intensify the entirety of the object at an equal or near equal sound intensity. A modification is to intensify selected portions of the object with greater intensity, such as, near the chest wall when imaging a human breast. It should be noted that in applications to human breast imaging, defining the location of the chest wall for purposes of orientation is of importance to the diagnostic process. This portion of the anatomy has the greatest thickness and thus requires a greater amount of sound intensity than other portions of the breast.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. An apparatus comprising:
 a transducer assembly means for generating an acoustic signal to pass through an object;
 a lens means for receiving an acoustic signal after it has passed through the object;
 a holographic image detection means for receiving the acoustic signal after it has passed through the lens; and
 electronic control means for causing the transducer assembly means to generate a plurality of pulses spaced from each other in time, the plurality of pulses forming a sequence of pulses, each pulse having selected characteristic parameters within the pulse itself and a plurality of the pulses in the sequence having different characteristic parameters from other pulses in the same sequence.

2. The apparatus of claim 1 wherein the characteristic parameter is the amplitude and a plurality of the pulses in the sequence have a different amplitude from each other.

3. The apparatus of claim 1 wherein the characteristic parameter is the frequency and a plurality of pulses in the sequence have a different frequency from each other.

4. The apparatus of claim 3 wherein the frequency difference between a first pulse and a second pulse within the plurality of pulses of a sequence is the same as the frequency difference between the second pulse and a third pulse of the same sequence.

5. The apparatus of claim 3 wherein the frequency difference between a first pulse and a second pulse within the plurality of pulses of a sequence is different than the frequency difference between the second pulse and a third pulse of the same sequence.

6. A method generating an acoustic hologram comprising:
 generating a plurality of acoustic pulses;
 transmitting the plurality of acoustic pulses as a sequence of pulses through an object;
 varying a property of the acoustic pulse from one pulse to another pulse within the sequence of pulses passing through the object;
 receiving the sequence of pulses that have passed through the object; and
 creating an image for each pulse in the sequence that contains varying data based on the property of the pulse that was varied.

7. The method according to claim 6 in which the property varied from one pulse to another is the frequency of the acoustic wave of the pulse, each pulse being at a single acoustic frequency itself but at a different acoustic frequency from another pulse in the same sequence.

8. The method according to claim 7 wherein the difference in frequency from one pulse to another pulse is the same as the difference in frequency for each pulse within the sequence.

9. The method according to claim 7 wherein the difference in frequency from one pulse to a second pulse is different than the difference in frequency between any other two pulses within the sequence.

10. The method according to claim 7 wherein the difference in frequency between a first pulse and a second pulse within the sequence is different than the difference in frequency between a second pulse and a third pulse in the same sequence.

11. The method according to claim 7 wherein the difference in frequency between a first pulse in the sequence and the second pulse in the sequence is the same as the difference in frequency between the second pulse of the sequence and a third pulse in the same sequence.

12. The method according to claim 6 in which the property varied from one pulse to another pulse is the amplitude of the acoustic wave of the pulse, each pulse being at a different amplitude from another pulse in the same sequencer.

13. The method according to claim 6 further including:

rotating a source of the acoustic pulses during generation of the sequence of acoustic pulses;

varying the point within the angle of rotation of the generation of the acoustic pulse from one pulse to another pulse within the sequence of pulses in order to vary the property of the acoustic pulse from one pulse to another within the sequence of pulses.

14. The method according to claim 13 further including:

transmitting each pulse at a different rotational position during the generation of the plurality of the acoustic pulses.

15. The method according to claim 13 further including:

generating each sequence of pulses having a plurality of acoustic pulses at the same relative angle for each sequence.

* * * * *